(12) United States Patent
Olek (10) Patent No.: US 11,761,041 B2
(45) Date of Patent: Sep. 19, 2023

(54) PARK2 AS EPIGENETIC MARKER FOR THE IDENTIFICATION OF IMMUNE CELLS, IN PARTICULAR MONOCYTES

(71) Applicant: Precision for Medicine GmbH, Berlin (DE)

(72) Inventor: Sven Olek, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 0 days.

(21) Appl. No.: 15/752,060

(22) PCT Filed: Sep. 22, 2016

(86) PCT No.: PCT/EP2016/072594
§ 371 (c)(1),
(2) Date: Feb. 12, 2018

(87) PCT Pub. No.: WO2017/050925
PCT Pub. Date: Mar. 30, 2017

(65) Prior Publication Data
US 2018/0216184 A1 Aug. 2, 2018

(30) Foreign Application Priority Data
Sep. 25, 2015 (GB) ...................... 1516975

(51) Int. Cl.
*C12Q 1/6881* (2018.01)
(52) U.S. Cl.
CPC ..... *C12Q 1/6881* (2013.01); *C12Q 2600/154* (2013.01)
(58) Field of Classification Search
CPC combination set(s) only.
See application file for complete search history.

(56) References Cited

U.S. PATENT DOCUMENTS

| 2007/0269823 A1* | 11/2007 | Huehn ............ | C12Q 1/6886 435/6.16 |
| 2013/0102483 A1* | 4/2013 | Dimitrova ....... | C12Q 1/6886 506/9 |

FOREIGN PATENT DOCUMENTS

| EP | 2248913 A1 | 11/2010 | |
| WO | 2011128820 A2 | 10/2011 | |
| WO | 2013033627 A2 | 3/2013 | |
| WO | 2014170497 A2 | 10/2014 | |
| WO | WO-2014170497 A2 * | 10/2014 | ........... C12Q 1/6881 |

OTHER PUBLICATIONS

May et al (Science (1988) vol. 241, p. 1441).*
Benner et al (Trends in Genetics (2001) vol. 17, pp. 414-418).*
Ehrlich et al. (2002 Oncogene vol. 21 p. 5400).*
Walsh et al teaches (Genes & Development (1999) vol. 13, pp. 26-36).*
Brooks et al. ( Cancers Causes control (2009) vol. 20, pp. 1539-1550).*
Sabbioni et al (Mol Diagn 7(3):201-207 [2003]).*
Zhang (PLOS Genetics (2009) vol. 5, e1000438).*
Harrison (Frontiers in Genetics (2011) vol. 2, article 74, pp. 1-13).*
Agirre (Int J Cancer (2006) voule 118, pp. 1945-1953).*
GenBank Accession NG_008289.1, *Homo sapiens* parkin RBR E3 ubiquitin protein ligase (PARK2), RefSeqGene on chromosome 6, (https://www.ncbi.nlm.nih.gov/nuccore/194440663?sat=18&satkey=3729738, Mar. 3, 2014).*
Zhao (Bone marrow and the control of immunity (2011) vol. 9, p. 9-11).*
Hughes (Arthritis and Rheumatology (Jun. 2014) vol. 66, pp. 1648-1658).*
Capello (British Journal of Haematology, 148, 245-255 (2009)).*
Pabinger (Biomolecular Detection and Quantification (2014)vol. 1, pp. 23-33).*
VanGuilder (BioTechniques vol. 44, Issue 5, Apr. 2008, pp. 619-626).*
Agirre, X. et al., "Abnormal methylation fo the common PARK2 and PACRG promoter is associated with downregulation of gene expression in acute lymphoblastic leukemia and chronic myeloid leukemia." Int. J. Cancer, 2006, 118(8): 1945-1953.
Handa, H. et al., "Methylation and Hydroxymethylation Status of Tumor Suppressor Genes and Common Fragile Sites Genes in Acute Myeloid Leukemia." Blood, 2014, 124: Abstract.

* cited by examiner

*Primary Examiner* — Steven Pohnert
(74) *Attorney, Agent, or Firm* — BakerHostetler (57) ABSTRACT

The present invention relates to a method, in particular an in vitro method, for identifying monocytes, comprising analyzing the methylation status of at least one CpG position in the mammalian gene region for parkin RBR E3 ubiquitin protein ligase (PARK2), wherein a de-methylation or lack of methylation of said gene region is indicative for a monocyte, when compared to a non-monocyte cell. The analyses according to the invention can identify monocytes on an epigenetic level and distinguish them from all other cells in complex samples, such as, for example, other blood or immune cells. The present invention furthermore provides an improved method for quantifying monocytes, in particular in complex samples. The method can be performed without a step of purifying and/or enriching cells, preferably in whole blood and/or non-trypsinized tissue. Also claimed are kits and specific oligonucleotides for use as primers or probes.

18 Claims, 2 Drawing Sheets
Specification includes a Sequence Listing.

TpG-Specific PCR system

FIG. 2B

CpG-Specific PCR system

SEQUENCE LISTING

<160> NUMBER OF SEQ ID NOS: 11

<210> SEQ ID NO 1
<211> LENGTH: 468
<212> TYPE: DNA
<213> ORGANISM: Homo sapiens

<400> SEQUENCE: 1

```
gagcaacttg cctggaagag gaggaaatga aaccgggcct tgacgacct  gccaagggcc    60
atttctgctg ccccagagca aaccttcgca cacaagctga gtgccttgga aacgcactgc   120
agagggggcgg gtgctgtcct ggcactgact cagcttttca cagcgcaagg ccgagcccga   180
acgacgcgct ggctttaatg gagatctgtc gcagccgttc catcccatct gcacatccac   240
ttaggcggcg ggtccagggt catggattca agagaagtgg catcaaacct gctttactta   300
aaccaacaag cagttcagaa aatacactcc caaataaccg gggatctaga tctccgggaa   360
taataaatta cacccatctc ccaatactgg gactgcattt gtgtgtgaag gcagtcaatg   420
gctgagagac ggctctgcgg tgagatgctg gggcaaaata gatcaaaa            468
```

<210> SEQ ID NO 2
<211> LENGTH: 468
<212> TYPE: DNA
<213> ORGANISM: Homo sapiens

<400> SEQUENCE: 2

```
aaacaactta cctaaaaaaa aaaaaaataa aaccaaacct ttaacaacct accaaaaacc    60
atttctacta ccccaaaaca aaccttcaca cacaaactaa ataccttaaa aacacactac   120
```

```
aaaaaaacaa atactatcct aacactaact caacttttca caacacaaaa ccaaacccaa    180
acaacacact aactttaata aaaatctatc acaaccattc catcccatct acacatccac    240
ttaaacaaca aatccaaaat cataaattca aaaaaaataa catcaaacct actttactta    300
aaccaacaaa caattcaaaa aatacactcc caaataacca aaaatctaaa tctccaaaaa    360
taataaatta cacccatctc ccaatactaa aactacattt atatataaaa acaatcaata    420
actaaaaaac aactctacaa taaaatacta aaacaaaata aatcaaaa                468
```

<210> SEQ ID NO 3
<211> LENGTH: 468
<212> TYPE: DNA
<213> ORGANISM: Homo sapiens

<400> SEQUENCE: 3

```
aaacaactta cctaaaaaaa aaaaaaataa aaccgaacct ttaacgacct accaaaaacc     60
atttctacta ccccaaaaca aaccttcgca cacaaactaa ataccttaaa aacgcactac    120
aaaaaaacga atactatcct aacactaact caacttttca caacgcaaaa ccgaacccga    180
acgacgcgct aactttaata aaaatctatc gcaaccgttc catcccatct acacatccac    240
ttaaacgacg aatccaaaat cataaattca aaaaaaataa catcaaacct actttactta    300
aaccaacaaa caattcaaaa aatacactcc caaataaccg aaaatctaaa tctccgaaaa    360
taataaatta cacccatctc ccaatactaa aactacattt atatataaaa acaatcaata    420
actaaaaaac gactctacga taaaatacta aaacaaaata aatcaaaa                468
```

<210> SEQ ID NO 4
<211> LENGTH: 22
<212> TYPE: DNA
<213> ORGANISM: Homo sapiens

<400> SEQUENCE: 4

```
gagtaatttg tttggaagag ga                                             22
```

<210> SEQ ID NO 5
<211> LENGTH: 23
<212> TYPE: DNA
<213> ORGANISM: Homo sapiens

<400> SEQUENCE: 5

```
ttttaatcta ttttaccccca aca                                           23
```

<210> SEQ ID NO 6
<211> LENGTH: 24
<212> TYPE: DNA
<213> ORGANISM: Homo sapiens

<400> SEQUENCE: 6

```
actaactcaa cttttcacaa caca                                           24
```

<210> SEQ ID NO 7
<211> LENGTH: 20
<212> TYPE: DNA
<213> ORGANISM: Homo sapiens

<400> SEQUENCE: 7

```
agatgggatg gaatggttgt                                                20
```

```
<210> SEQ ID NO 8
<211> LENGTH: 26
<212> TYPE: DNA
<213> ORGANISM: Homo sapiens

<400> SEQUENCE: 8
agtgtgttgt ttgggtttgg ttttgt                                          26

<210> SEQ ID NO 9
<211> LENGTH: 26
<212> TYPE: DNA
<213> ORGANISM: Homo sapiens

<400> SEQUENCE: 9
acacaaacta aataccttaa aaacgc                                          26

<210> SEQ ID NO 10
<211> LENGTH: 16
<212> TYPE: DNA
<213> ORGANISM: Homo sapiens

<400> SEQUENCE: 10
gggatggaac ggttgc                                                     16

<210> SEQ ID NO 11
<211> LENGTH: 22
<212> TYPE: DNA
<213> ORGANISM: Homo sapiens

<400> SEQUENCE: 11
cgcaaaaccg aacccgaacg ac                                              22
```

PARK2 AS EPIGENETIC MARKER FOR THE IDENTIFICATION OF IMMUNE CELLS, IN PARTICULAR MONOCYTES

CROSS REFERENCE TO RELATED APPLICATIONS

This application is a National Stage Application of International Application Number PCT/EP2016/072594, filed Sep. 22, 2016; which claims priority to Great Britain Patent Application No. 1516975.8, filed Sep. 25, 2015.

The Sequence Listing for this application is labeled "SeqList-12Feb18-ST25.txt", which was created on Feb. 12, 2018, and is 4 KB. The entire content is incorporated herein by reference in its entirety.

The present invention relates to a method, in particular an in vitro method, for identifying monocytes, comprising analyzing the methylation status of at least one cytosine-phosphodiester-guanine (CpG) position in the mammalian gene region for parkin RBR E3 ubiquitin protein ligase (PARK2), wherein a demethylation or lack of methylation of said gene region is indicative for a monocyte, when compared to a non-monocyte cell. The analyses according to the invention can identify monocytes on an epigenetic level and distinguish them from all other cells in complex samples, such as, for example, other blood or immune cells. The present invention furthermore provides an improved method for quantifying monocytes, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure monocytes of the blood within any solid organs or tissue or any body fluid of a mammal.

BACKGROUND OF THE INVENTION

Monocytes are a type of white blood cells (leukocytes). They are the largest of all leukocytes. They are part of the innate immune system of vertebrates including all mammals (humans included), birds, reptiles, and fish. They are amoeboid in shape, having a granulated cytoplasm. They play multiple roles in immune function. Such roles include: (1) replenishing resident macrophages under normal states, and (2) in response to inflammation signals, monocytes can move quickly to sites of infection in the tissues and divide/differentiate into macrophages and dendritic cells to elicit an immune response.

There are at least two types of monocytes in human blood, the "classical" monocyte is characterized by high level expression of the CD14 cell surface receptor (CD14++ CD16− monocyte). The "non-classical" monocyte shows low level expression of CD14 and additional coexpression of the CD16 receptor (CD14+CD16++ monocyte).

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics-heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfate sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

WO 00/31253 relates to nucleic acids coding for mutated or truncated forms of the human parkin gene, or forms comprising multiplication of exons, and the corresponding proteins and antibodies. Disclosed are methods and kits for identifying mutations of the parkin gene, and for studying compounds for therapeutic purposes.

De Mena et al. (in: De Mena et al. No differential DNA methylation of PARK2 in brain of Parkinson's disease patients and healthy controls. Mov Disord. 2013 December; 28(14):2032-3. Epub 2013 Jul. 18 disclose no epigenetic changes in PARK2 in Parkinson's Disease.

Poulogiannis et al. (in: Poulogiannis et al. PARK2 deletions occur frequently in sporadic colorectal cancer and accelerate adenoma development in Apc mutant mice. Proc Natl Acad Sci USA. 2010 Aug. 24; 107(34):15145-50. Epub 2010 Aug. 9., 2014 Mar. 5; 15(3)) disclose that in 100 primary colorectal carcinomas, 33% show DNA copy number (DCN) loss involving PARK2, the gene encoding PARKIN, the E3 ubiquitin ligase whose deficiency is responsible for a form of autosomal recessive juvenile parkinsonism. PARK2 is located on chromosome 6 (at 6q25-27), a chromosome with one of the lowest overall frequencies of DNA copy number alterations recorded in colorectal cancers. Evidence of some PARK2 mutations and promoter hypermethylation is described. They conclude that PARK2 is a tumor suppressor gene whose haploinsufficiency cooperates with mutant APC in colorectal carcinogenesis.

In view of the above, it is an object of the present invention to provide an improved and in particular robust method based on DNA-methylation analysis as a superior tool in order to more conveniently and reliably detect, identify, discriminate, and quantify monocytes.

The present invention solves the above object by providing method for identifying monocytes in a sample, comprising analyzing the methylation status (bisulfite convertibility) of at least one CpG position in the mammalian (e.g. human) gene region for parkin RBR E3 ubiquitin protein ligase (PARK2), wherein preferably said gene region as analyzed is positioned based on/according to SEQ ID NO: 1, wherein a demethylation or lack of methylation of said gene region is indicative for a monocyte, in particular a classical monocyte, when compared to a non-monocyte cell.

The parkin RBR E3 ubiquitin protein ligase (PARK2, or AR-JP, parkin, PDJ) gene, one of the largest human genes, provides instructions for making a protein called parkin. Parkin plays a role in the cell machinery that breaks down (degrades) unneeded proteins by tagging damaged and excess proteins with molecules called ubiquitin. Ubiquitin serves as a signal to move unneeded proteins into specialized cell structures known as proteasomes, where the proteins are degraded. Researchers have identified more than 200 PARK2 gene mutations that cause Parkinson disease. The gene for human PARK2 is found on chromosome 6, 161,347,420-162,727,771 reverse strand., Ensembl-ID: ENSG00000185345.

In the context of the present invention, the gene region shall comprise all of the genomic region relating to and encoding for PARK2. Thus, included are enhancer regions, promoter region(s), introns, exons, and non-coding regions (5'- and/or 3'-regions) that belong to PARK2. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the PARK2 gene by the inventors, as specific epigenetic marker, allowing the identification of monocytes as well as the clinical routine application of said analysis.

In the context of the present invention, the genomic region of PARK2, in particular according to SEQ ID NO: 1 allows the identification of monocytes. Surprisingly, the discriminatory pattern of bisulfite convertible and non-convertible cytosine is particularly and even exclusively limited to the genomic region according to SEQ ID NO:1 for monocytes as shown using the amplicon according to SEQ ID NO:1, and in particular in the bisulfite converted sequences according to SEQ ID NOs: 2 and/or 3.

The inventors could demonstrate that in the monocytes the CpG motifs as disclosed are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify monocytes, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of monocytes without purification or any staining procedures.

Another preferred aspect of the method according to the present invention then further comprises a quantification of the relative amount of monocytes based on comparing relative amounts of said methylation frequency in the region as analyzed with relative amounts of the methylation frequency in a control gene, such as, for example, human glyceraldehyde 3-phosphate dehydrogenase (GAPDH). Said quantification is thus achieved based on the ratio of the bisulfite convertible DNA to non-convertible DNA in the genetic region of PARK2 (e.g. of SEQ ID NO: 1) as described and analyzed herein. Most preferred is a quantification of the relative amount of monocytes is based on an (preferably parallel or simultaneous) analysis of the relative amount of bisulfite convertible DNA of cell-specific region for PARK2, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 1, preferably oligomers according to any of SEQ ID NOs: 2 to 4.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the methylation-specific PCR (MSP), HEAVYMETHYL™, SCORPION™, methylation-sensitive single-nucleotide primer extension (MS-SNUPE), METHYLLIGHT™, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the PARK2 gene region is produced that is a particularly preferred "tool" for performing the method(s) according to the present invention. Consequently, oligomers according to any of SEQ ID NOs: 4 and 5 or an amplicon as amplified by a primer pair based on SEQ ID NOs: 4 and 5 or 6 and 7 or 9 and 10 as mentioned herein constitute preferred embodiments of the present invention. Thus, the sequences of SEQ ID NOs: 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID NO: 1. Amplification can take place either in the genomic and/or bisulfite (i.e. "converted") DNA sequence.

Figure 1:
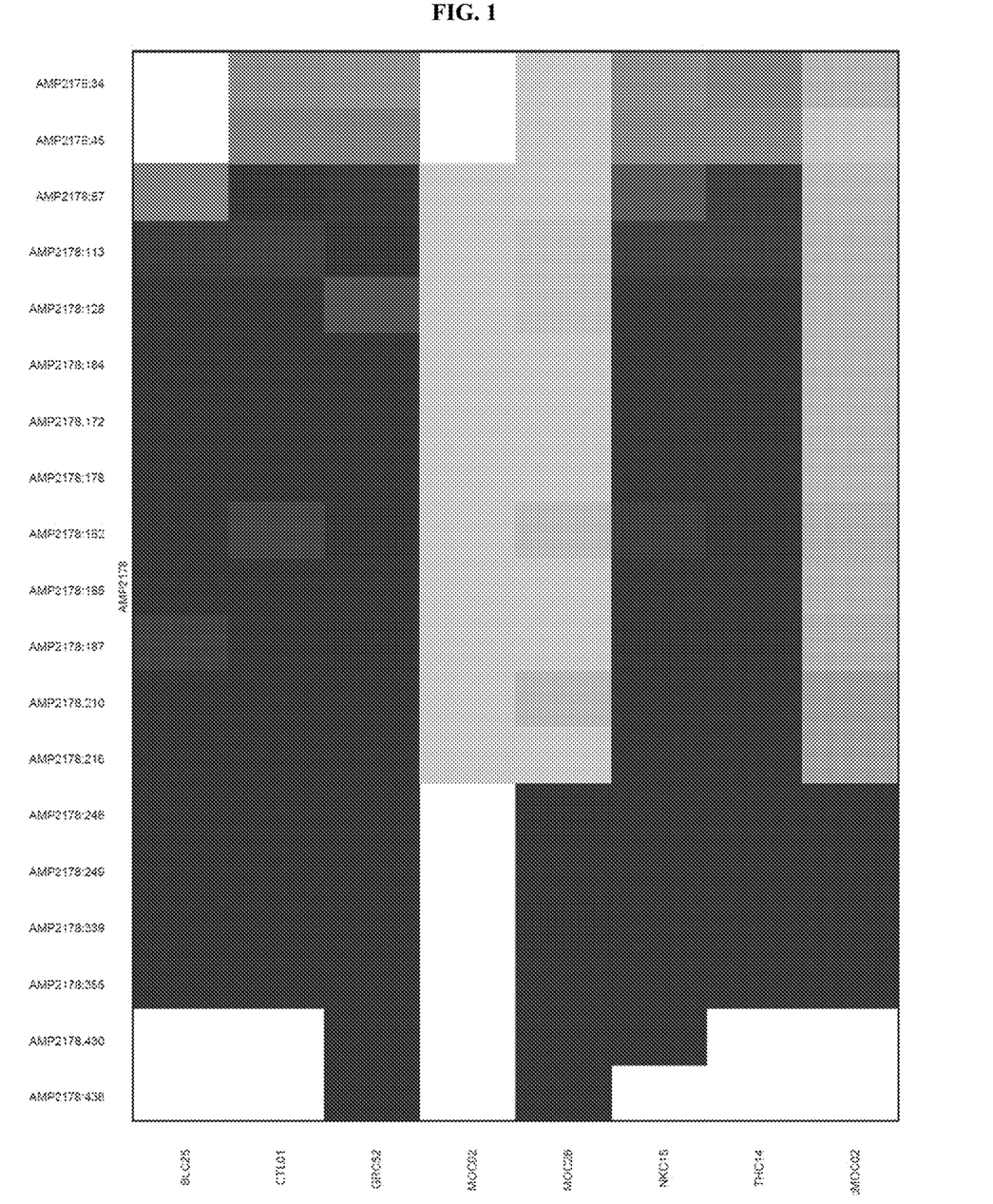

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 1, 2, 3, 4, 5, 6, 7, 8, 9, 10, 11, 12, 13, 14, 15, 16, 17, 18, and 19 in the amplicon No. 2178 according to SEQ ID NO: 1. The positions are numerically counted from the 5'-end of an amplicon as generated and analyzed, and are designated as 34, 45, 87, 113, 128, 164, 172, 178, 182, 185, 187, 210, 216, 246, 249, 339, 355, 430, and 438 in FIG. 1. Preferred are combinations of 1, 2, 3, 4, 5, 6, 7, 8, 9, 10, 11, 12 or 13 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 6, 7, 8, 9, 10, 11, 12 and/or 13 in the amplicon No. 2178 of the PARK2 specific bisulfite convertible region (SEQ ID NO: 1), or all sites as present on the bisulfite convertible region according to SEQ ID NO: 1.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, methylation-specific PCR (MSP), HEAVYMETHYL™, METHYLLIGHT™, methylation-sensitive single-nucleotide primer extension (MS-SNUPE), or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said monocytes from all major peripheral blood cell types and/or non-blood cells, preferably, but not limited to, from follicular helper T cells, cytotoxic T-cells, granulocytes, B cells, NK-cells, and T-helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said monocytes. The monocytes can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of monocytes in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said monocytes as e.g. a sample for cell transfer into a patient.

Another preferred aspect of the method according to the present invention then relates to a method as above, further comprising formulating said monocytes as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NOs: 4 to 11, or an amplicon according to SEQ ID NOs: 1 to 3.

Yet another preferred aspect of the present invention then relates to a kit for identifying, quantifying, and/or monitoring monocytes in a mammal based on the analysis of the bisulfite accessibility of CpG positions in the gene region of PARK2, comprising components for performing a method according to invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NOs: 4 to 11.

The present invention also encompasses the use of oligomers or amplicon or a kit according to the present invention for identifying and/or for monitoring monocytes in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$(C and/or mC and/or hmC and/or fC and/or cC)
$b=\Sigma$(C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the PARK2 genetic region and in particular the amplicon as described herein as a marker, the inventors very specifically identified, quantified and particularly differentiated monocytes, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

FIG. 1 shows the analysis of CpG sites on amplicon No. 2178 (SEQ ID NO: 1) according to the invention. The horizontal boxes in the table correspond to the CpG positions in the amplicon as analyzed (e.g. CpG 1, 2, etc.) with the positions indicated (34, 45, 87, 113, 128, 164, 172, 178, 182, 185, 187, 210, 216, 246, 249, 339, 355, 430, and 438, corresponding to CpG 1, 2, . . . etc.), and the columns correspond to the cell types as analyzed. The abbreviations at the bottom indicate BLC25=B-lymphocytes; CTL01=CD8$^+$ cytotoxic T-cells; GRC52=granulocytes; MOC02, MOC26=CD14$^+$ monocytes; NKC15=CD56$^+$ NK-cells; and THC14=CD4$^+$ Helper T-cells, ncMOC02="non-classical" CD16$^+$ monocytes, respectively.

SEQ ID NO: 1 shows the genomic sequence of amplicon AMP2178 according to the present invention.

SEQ ID NOs: 2 and 3 show the sequences of bisulfate-converted target-regions of preferred qPCR-assay-systems of the invention.

SEQ ID NOs: 4 to 11 show the sequences of specific oligomers (primers and probes) according to the present invention.

EXAMPLES

Example 1

In order to identify monocytes, qPCR was performed on bisulphite converted samples stemming from the human genomic region according to the following sequence (AMP2178, SEQ ID NO: 1), relevant CpGs are shaded in gray:

```
GAGCAACTTGCCTGGAAGAGGAGGAAATGAAACCGGGCCTTTGACCGACCTGCCAAGGGCCATTTCTGCTGCCCCA

GAGCAAACCTTCGCACACAAGCTGAGTGCCTTGGAAACGCACTGCAGAGGGGCCGGTGCTGTCCTGGCACTGACT

CAGCTTTTCACAGCGCAAGGCCGAGCCCGAACGACGCGCTGGCTTTAATGGAGATCTGTCGCAGCCGTTCCATCC

CATCTGCACATCCACTTAGGCGGCGGGTCCAGGGTCATGGATTCAAGAGAAGTGGCATCAAACCTGCTTTACTTA

AACCAACAAGCAGTTCAGAAAATACACTCCCAAATAACCGGGGATCTAGATCTCCGGGAATAATAAATTACACCC

ATCTCCCAATACTGGGACTGCATTTGTGTGTGAAGGCAGTCAATGGCTGAGAGACGGCTCTGCGGTGAGATGCTG

GGGCAAAATAGATCAAAA
```

For the actual epigenetic profiling of the amplicon region in blood cell subtypes, the immune cell populations as analyzed were as follows (see FIG. 1)
BLC25=B-lymphocytes
CTL01=CD8[+] cytotoxic T-cells
GRC52=granulocytes
MOC02, MOC26=CD14[+] monocytes
NKC15=CD56[+] NK-cells
THC14=CD4[+] Helper T-cells
ncMOC02="non-classical" CD16[+] monocytes The bisulfite-converted target-regions of preferred qPCR-assay-system as developed were:

```
TpG-specific (SEQ ID NO. 2):
AAACAACTTACCTAAAAAAAAAAAAATAAAACCRAACCTTTAACRACCTACCAAAAACCATTTCTACTACCCCA

AAACAAACCTTCACACACAAACTAAATACCTTAAAAACACACTACAAAAAACRAATACTATCCTAACACTAACT

CAACTTTTCACAACACAAAACCRAACCRAACRACRCACTAACTTTAATAAAAATCTATCACAACRATTCCATCC

CATCTACACATCCACTTAAACRACRAATCCAAAATCATAAATTCAAAAAAAATAACATCAAACCTACTTTACTTA

AACCAACAAACAATTCAAAAAATACACTCCCAAATAACCRAAAATCTAAATCTCCRAAAATAATAAATTACACCC

ATCTCCCAATACTAAAACTACATTTATATATAAAAACAATCAATAACTAAAAAACAACTCTACRATAAAATACTA

AAACAAAATAAATCAAAA

CpG-specific: (SEQ ID NO. 3):
AAACAACTTACCTAAAAAAAAAAAAATAAAACCGAACCTTTAACGACCTACCAAAAACCATTTCTACTACCCCA

AAACAAACCTTCGCACACAAACTAAATACCTTAAAAACGCACTACAAAAAAACGAATACTATCCTAACACTAACT

CAACTTTTCACAACGCAAAACCGAACCCGAACGACGCGCTAACTTTAATAAAAATCTATCGCAACCGTTCCATCC

CATCTACACATCCACTTAAACGACGAATCCAAAATCATAAATTCAAAAAAAATAACATCAAACCTACTTTACTTA

AACCAACAAACAATTCAAAAAATACACTCCCAAATAACCGAAAATCTAAATCTCCGGAAAATAATAAATTACACCC

ATCTCCCAATACTAAAACTACATTTATATATAAAAACAATCAATAACTAAAAAACGACTCTACGGATAAAATACTA

AAACAAAATAAATCAAAA
```

The respective sequence of the assay-target region is underlined.

The following primers and probes were used for the qPCR:

| | | |
|---|---|---|
| Forward amplification primer | 2178r | GAGTAATTTGTTTGGAAGAGGA (SEQ ID No. 4) |

| | | |
|---|---|---|
| Reverse amplification primer | 2178q | TTTTAATCTATTTTACCCCAACA (SEQ ID No. 5) |
| Forward primer TpG-specific | 2178r_T_fw | ACTAACTCAACTTTTCACAACACA (SEQ ID No. 6) |
| Reverse primer TpG-specific | 2178q_T_rev | AGATGGGATGGAATGGTTGT (SEQ ID No. 7) |
| Probe TpG-specific | 2178_TP | AGTGTGTTGTTTGGGTTTGGTTTTGT (SEQ ID No. 8) |
| Forward primer CpG-specific | 2178r_C_fw | ACACAAACTAAATACCTTAAAAACGC (SEQ ID No. 9) |
| Reverse primer CpG-specific | 2178q_C_rev | GGGATGGAACGGTTGC (SEQ ID No. 10) |
| Probe CpG-specific | 2178_CP | CGCAAAACCGAACCCGAACGAC (SEQ ID No. 11) |

Figure 2A:
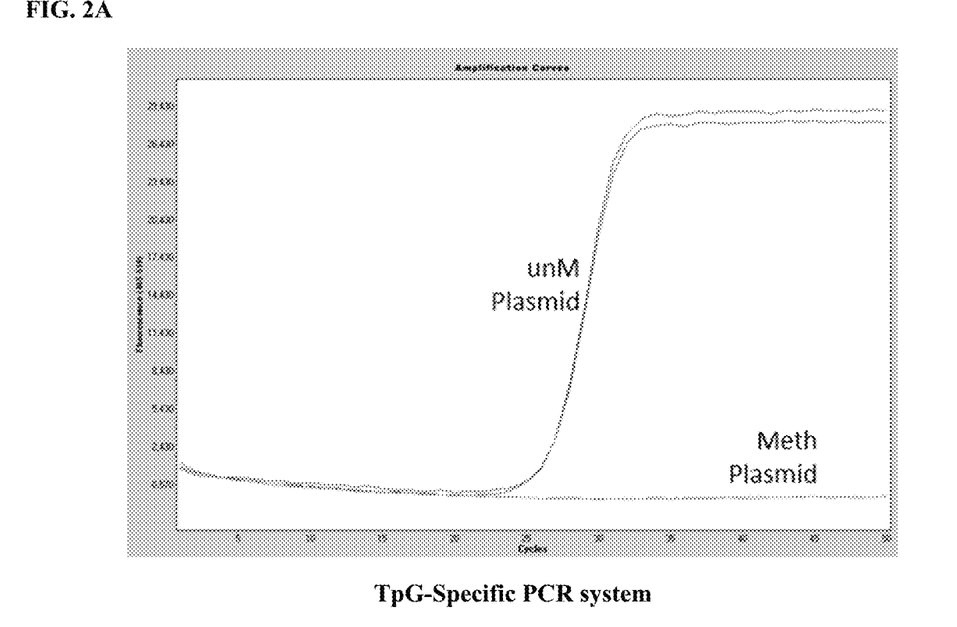
FIGS. 2A-2B are series of graphs depicting the specificity of the TpG-specific PCR-system using un-methylated and methylated plasmid-DNA test-template (FIG. 2A) and the specificity of the CpG-specific PCR-system using un-methylated and methylated plasmid-DNA test-template (FIG. 2B).
Figure 2B:
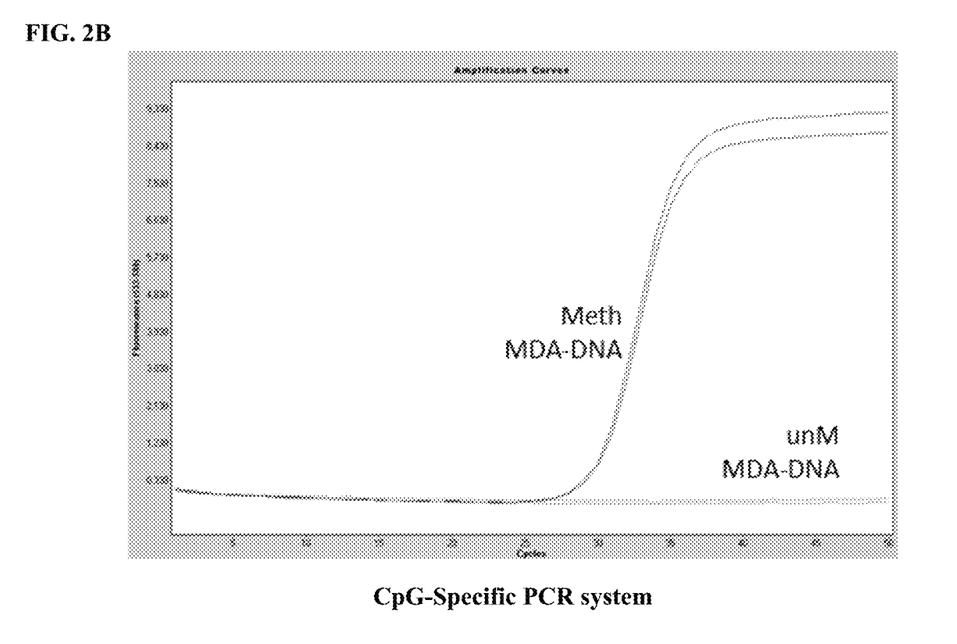

The specificity of the TpG-specific PCR-system was demonstrated using test-templates (plasmid-DNA) as shown in FIGS. 2A-2B.

The cell type specificity (as measured by qPCR) was found as follows:

| Cell type | Description | TpG-copies PARK2 | GAPDH-copies | Demethylation (%) |
|---|---|---|---|---|
| CTL-Pool | CD8+ CTLs | 34.9 | 1823.3 | 1.9 |
| CTL15A | | 0.7 | 490.0 | 0.2 |
| THC05 | CD4+ Th-cells | 13.2 | 221.3 | 6.0 |
| THC13A1 | | 6.0 | 1606.7 | 0.4 |
| MOC06 | CD14+ Monocytes | 1150.0 | 852.3 | 134.9 |
| MOC28A1 | | 3076.7 | 2273.3 | 135.3 |
| NKT-Pool | CD8+CD56+ NKT | 9.5 | 2283.3 | 0.4 |
| BLC27A1 | CD19+ B-cells | 3.5 | 1550.0 | 0.2 |
| NKC25A | CD56+ NK | 14.2 | 2103.3 | 0.7 |

The invention claimed is:

1. A method for producing and detecting an amplicon from a bisulfite treated human parkin RBR E3 ubiquitin protein ligase (PARK2) genomic region, the method comprising: a) bisulfite treating isolated genomic DNA from human immune cells to convert unmethylated cytosines to uracils; b) amplifying a portion of the PARK2 genomic region from the bisulfite treated genomic DNA to produce an amplicon comprising cytosine-adenine (CA) at CA positions 172, 178, and 182 of SEQ ID NO: 2, and c) detecting the amplicon with a probe comprising the nucleic acid sequence of SEQ ID NO: 8.

2. The method according to claim 1, wherein said amplifying comprises amplifying an intron of said genomic region.

3. The method according to claim 1, further comprising detecting the CA by a method selected from a methylation specific enzymatic digest, bisulfite sequencing, promoter methylation, CpG island methylation, methylation specific polymerase chain reaction (MSP), methylation-sensitive single-nucleotide primer extension (Ms-SNuPE), and other methods relying on a detection of amplified DNA.

4. The method according to claim 1, wherein said human immune cells are from blood, a tissue, or an organ.

5. The method according to claim 1, wherein said method is performed without a step of purifying and/or enriching said human immune cells.

6. The method according to claim 1, wherein said human immune cells are from a human who suffers from or is likely to suffer from an autoimmune disease, transplant rejection, infection disease, cancer, and/or allergy.

7. The method of claim 1 performed using a kit comprising a) a bisulfate reagent, and b) materials for detecting the CA in the amplicon.

8. The method according to claim 1, wherein the amplifying comprises using an oligomer according to any of SEQ ID NOs: 4-7 and 9-11.

9. The method according to claim 1, wherein said amplicon comprises CA at CA positions 34, 45, 87, 113, 128, 164, 172, 178, 182, 185, 187, 210, and 216 of SEQ ID NO: 2.

10. The method according to claim 5, wherein the human immune cells are from whole blood and/or non-trypsinized tissue.

11. The method of claim 1, further comprising
d) detecting methylation status of all cytosine-phosphate-guanine (CpG) positions from the amplicon.

12. The method of claim 1, wherein the amplicon comprises SEQ ID NO: 2.

13. A method for producing and detecting an amplicon from a bisulfite treated human parkin RBR E3 ubiquitin protein ligase (PARK2) genomic region, the method comprising:
  a) bisulfite treating isolated genomic DNA from a human monocyte cell sample to convert unmethylated cytosines to uracils;
  b) amplifying with quantitative polymerase chain reaction (qPCR) a portion of the bisulfite treated genomic DNA to produce an amplicon comprising SEQ ID NO: 2 or 3, and
  c) detecting the amplicon with a probe comprising the nucleic acid sequence of SEQ ID NO: 8.

14. The method of claim 13, wherein the human monocyte cell sample is isolated from a human blood sample.

15. The method of claim 13, further comprising
   d) detecting methylation status of at least one cytosine-phosphate-guanine (CpG) position from the amplicon.

16. A method of producing and detecting an amplicon, the method comprising:
   a) bisulfite treating DNA from human immune cells to generate bisulfite treated DNA where unmethylated cytosines are converted to uracils,
   b) amplifying with quantitative polymerase chain reaction (qPCR) a region of the bisulfite treated DNA to produce an amplicon comprising nucleotides 165-190 of SEQ ID NO: 2 and having cytosine-adenine (CA) at CA positions 172, 178, 182, 185, and 187 relative to SEQ ID NO: 2, and
   c) detecting the amplicon with a probe comprising the nucleic acid sequence of SEQ ID NO: 8.

17. The method of claim 16, wherein the amplicon comprises nucleotides 144-230 of SEQ ID NO: 2.

18. The method of claim 17, wherein the amplicon comprises cytosine-adenine (CA) at positions 164, 172, 178, 182, 185, 187, 210, and 216 relative to SEQ ID NO: 2.

\* \* \* \* \*